United States Patent [19]

Yolles

[11] 4,206,301

[45] Jun. 3, 1980

[54] SUSTAINED FLAVOR RELEASE COMPOSITION

[76] Inventor: Seymour Yolles, 404 Stamford Dr., Newark, Del. 19711

[21] Appl. No.: 460,299

[22] Filed: Apr. 12, 1974

Related U.S. Application Data

[62] Division of Ser. No. 293,168, Sep. 28, 1972, Pat. No. 3,818,107.

[51] Int. Cl.$^2$ .................. A23L 1/04; C08B 11/20
[52] U.S. Cl. .......................... 536/3; 424/68; 426/3; 426/6; 426/533; 426/534; 426/538; 426/650; 426/651; 525/61; 525/326; 536/95
[58] Field of Search ............ 260/209.6, 91.3 PV, 260/885, 674 A, 66, 73 R, 231 A, 212, 73 I; 424/48; 426/3, 6, 533, 534, 538, 650, 651; 526/7, 9, 11, 12, 13, 16; 536/3, 95

[56] References Cited

U.S. PATENT DOCUMENTS

| | | | |
|---|---|---|---|
| 2,341,306 | 2/1944 | Agre et al. ................. 260/73 |
| 2,596,852 | 5/1952 | Heggie ..................... 260/85.7 |
| 2,740,772 | 4/1956 | Alfrey ..................... 260/86.1 E |
| 3,055,866 | 9/1962 | Oyanagi ..................... 260/73 |
| 3,140,184 | 7/1964 | Robbins ..................... 526/7 |
| 3,242,161 | 3/1966 | Borchert ..................... 260/209.6 |
| 3,255,018 | 6/1966 | Comollo ..................... 260/91.3 VA |
| 3,300,473 | 1/1967 | Christoffel et al. ........... 260/209 |
| 3,320,200 | 4/1967 | Kane ..................... 526/7 |
| 3,332,428 | 7/1967 | Mold et al. ................. 131/17 |
| 3,351,583 | 11/1967 | Bishop ..................... 260/231 A |
| 3,431,254 | 3/1969 | Klug ..................... 260/231 A |
| 3,548,408 | 12/1970 | Worrall ..................... 260/91.3 VA |
| 3,651,206 | 3/1972 | Litchfield et al. ............ 424/48 |
| 3,705,146 | 12/1972 | Smith ..................... 260/209 R |
| 3,737,398 | 6/1973 | Yamaguchi ................. 260/2.5 F |
| 3,749,766 | 7/1973 | Litchfield et al. ............ 424/48 |
| 3,761,286 | 9/1973 | Shepherd et al. ............. 426/6 |
| 3,795,744 | 3/1974 | Ogawa et al. ................. 426/3 |
| 3,826,847 | 7/1974 | Ogawa et al. ................. 426/3 |
| 3,857,964 | 12/1974 | Yolles ..................... 426/3 |
| 3,988,482 | 10/1976 | Higashiyama et al. ......... 426/534 |

OTHER PUBLICATIONS

Rose, The Condensed Chemical Dictionary, Reinhold Publishing Corporation, N.Y., N.Y., 1956, p. 498.
Webster's Third New International Dictionary, 1963, p. 867.

*Primary Examiner*—Ronald W. Griffin
*Attorney, Agent, or Firm*—David E. Brook

[57] ABSTRACT

Sustained flavor release compositions are disclosed which comprise polymer backbones having pendant flavor groups thereon. Such compositions can be used, for example, in chewing gums. Release of the flavor can be accomplished by hydrolysis upon mastication of the chewing gum.

In one embodiment, aldehyde flavors are reacted with polymers having hydroxy groups thereon to produce a polymer backbone with pendant acetal or hemi-acetal flavor groups. An example is the reaction product of cinnamic aldehyde and partially hydrolyzed polyvinyl acetate. In a like manner, ketone flavors can be reacted with similar polymers to form pendant ketal flavor groups. Also, alcohol flavors can be reacted with polymers having aldehyde or ketone groups to provide polymer backbones with pendant acetal or ketal moieties thereon.

3 Claims, No Drawings

SUSTAINED FLAVOR RELEASE COMPOSITION

This is a division of application Ser. No. 293,168, filed Sept. 28, 1972, now U.S. Pat. No. 3,818,107, issued June 18, 1974.

BACKGROUND OF THE INVENTION

1. Field of the Invention

This invention relates to sustained flavor release compositions and more particularly to sustained flavor release compositions formed by appending appropriate hydrolyzable flavor groups onto polymer backbones.

2. Description of the Prior Art

It is known that with most flavored chewing gums the perception of flavor drops off sharply after a short initial period of chewing. It has also been noted that large amounts of the flavor incorporated into chewing gums are retained and never perceived by the chewer. Therefore, for chewing gum and many other applications, it would be advantageous if the release of flavors could be controllably released continuously and at a desirable level over a predetermined period of time.

One approach used to achieve improved sustained release of flavors has been to encapsulate the flavors prior to their incorporation into chewing gum. Corbin, U.S. Pat. No. 3,201,353, discloses the use of microinclusions containing flavors for chewing gums. in another patent, Pilotti, U.S. Pat. No. 3,011,949, it is taught that the controlled release of active ingredients from slab chewing gum can be achieved by coating solid particles of active flavor ingredients with a sugar solution, drying the coating, pulverizing the coated particles and mixing the pulverized material with the other constituents of slab chewing gum. Other techniques have been to use gelatin-coacervated flavors (U.S. Pat. No. 2,886,449), gelatin encapsulated flavors (U.S. Pat. No. 2,886,446), or gelatin metaphosphate encapsulated microdroplets of flavors (U.S. Pat. No. 2,886,444), within an all-enveloping mass of chewable base. Despite the amount of research done to control the release of flavors by encapsulation techniques, none of the methods previously known has proven successful to date.

A different technique for producing sustained release of flavors is disclosed in Heggie, U.S. Pat. No. 2,596,852. By this method, permanently flavored gums are formed by using gum bases formed from vinyl acetate copolymerized with vinyl unsaturated flavors. This technique, however, is severely limited by the number of vinyl unsaturated flavors available, and also because incorporation of flavors into the polymer chain tends to destroy the flavor producing characteristics of the flavor monomer. That is, once incorporated as part of the polymer via vinyl polymerization, the flavor molecule is so altered as to become an inseparable part of the polymer.

There is a great need, therefore, for new flavors capable of controllable sustained release.

SUMMARY OF THE INVENTION

This invention relates to sustained flavor release compositions comprising polymer backbones with flavor groups appended thereon. Such pendant flavor moieties are releasable from the polymer backbone by hydrolysis. Suitable hydrolysis conditions can be achieved, for example, upon mastication of chewing gums containing the new flavors.

Some types of pendant flavor groups included within the scope of this invention are acetal, hemiacetal, and ketal groups. Many common flavors are either aldehydes, ketones or alcohols and thus lend themselves to preparation of these flavor groups.

The flavor groups can be produced directly by reacting an aldehyde or ketone flavor with polymers containing hydroxy groups, or the pendant groups can be produced by first forming acetal flavor groups and subsequently grafting these onto various polymer backbones.

Still other flavors comprise alcohols. Alcohol flavors can be appended onto polymer backbones using polymers with pendant orthoester groups wherein the alcohol moiety of the orthoester group is the flavor, or by treating a polymer having appended aldehyde or keto groups with the alcohol flavor.

Since a chemical system rather than a mechanical encapsulation technique is used to bind the flavors, a great deal of flexibility in the rate and duration of flavor release can be obtained. Further, the lumpy texture often produced by introducing encapsulated particles into chewing gum or other products is avoided. On the other hand, the compositions produced by using this invention release flavors easily and efficiently.

DESCRIPTION OF THE INVENTION

A first class of sustained flavor release compositions comprises those wherein acetal, hemiacetal, or ketal flavor groups are formed on polymer backbones. Several techniques can be used to prepare this class of materials.

Acetal and hemiacetal flavor groups can be tacked directly onto certain suitable polymers. To accomplish this, aldehyde flavors are reacted with polymers containing pendant hydroxy groups to produce the corresponding acetal or hemiacetal flavor groups. Included among suitable polymers are partially hydrolyzed polyvinyl acetate, partially hydrolyzed copolymers of polyvinyl acetate and polyvinyl alcohol, hydroxy propyl cellulose, hydroxy propyl alginates, etc. To be suitable, of course, both the aldehyde flavors and backbone polymers must, of course, be physiologically inert. In addition, if the flavor is to be used in chewing gum, the polymer should be one that is chewable or compatible with chewing gum bases. Such polymers normally have molecular weights between about 2,000 and 20,000, and are well known to those skilled in the art.

The above technique is specifically illustrated by use of the following structural formulas:

1. Formation

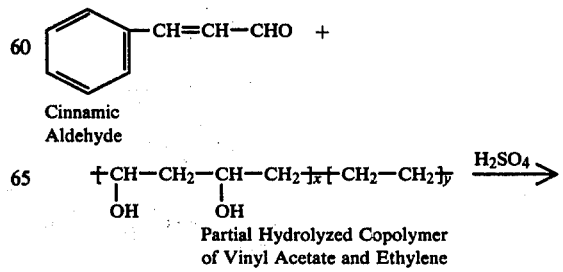

-continued

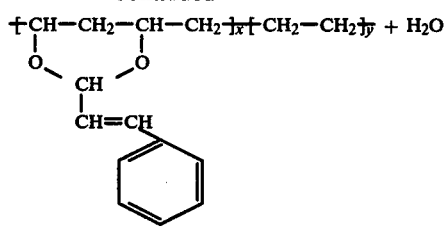

Polymer with Pendant Cinnamic
Cyclic Acetal Flavor Group

2. Hydrolysis

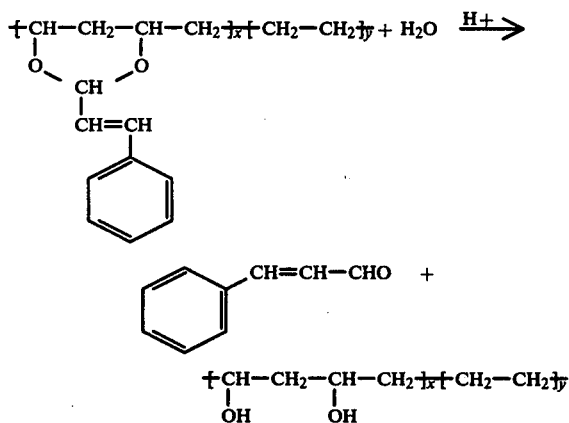

In a second method of preparing acetal and Ketal pendant flavor groups, epichlorohydrin or epibromohydrin is used. The aldehyde or ketone flavor is reacted with epichloro- or epibromohydrin to produce a chloro- or bromopropyl ketal or acetal. This can then be reacted with polymers having sodium metal ions associated therewith. Suitable polymers include sodium alginate, sodium starch, sodium carboxymethylcellulose, copolymers of sodium polyacrylates, salts of pectin and pectic acid, etc.

This method of preparing pendant acetal and ketal flavor groups can be specifically illustrated with the use of the following structural formulas:

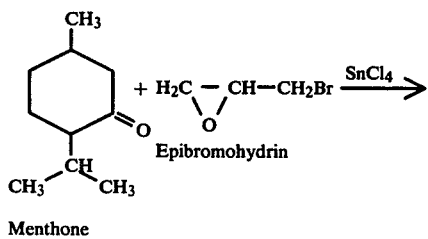

Epibromohydrin

Menthone

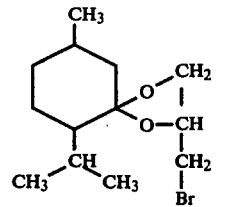

Ketal Formed from Menthone
and Epibromohydrin

-continued

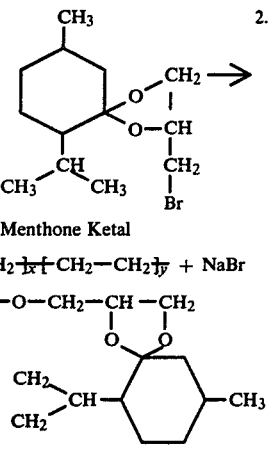

Sodium Salt of a
Copolymer of Acrylic
Acid and Ethylene

Menthone Ketal

Copolymer with Pendant
Menthone Ketal

A second indirect method for producing the acetal or ketal flavor groups and subsequently grafting them onto polymer backbones is as follows. In this method, an aldehyde or ketone flavor is reacted with a polyhydric alcohol such as glycerine to produce the corresponding acetal or ketal of the flavor with an extra pendant hydroxide group. The acetal or ketal flavor is then reacted with a polymer having pendant esters of carboxylic acid groups. In this method, basic catalysts such as lithium methoxide and lithium hydride are used. It is important to be able to use these basic catalysts, and that is why the ester of the carboxylic acid is used rather than the free acid, because acidic catalysts such as sulfuric acid, although capable of catalyzing such alcoholyses, also catalyse the opening and breaking of the cyclic acetal flavors. Thus, the flavor acetal or ketal groups can be destroyed if basic catalysts are not used.

This method is illustrated specifically with the following structural formulas:

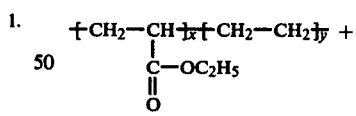

Copolymer of Ethyl
Acrylate and Ethylene

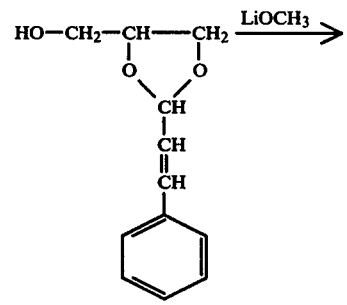

Cyclic Acetal of Glycerine
and Cinnamic Aldehyde

-continued

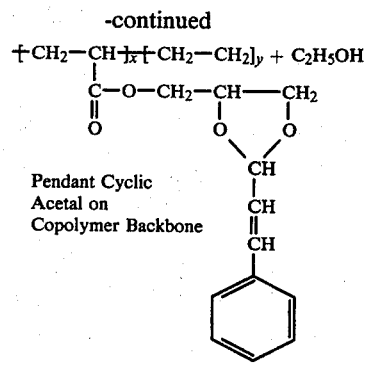

Pendant Cyclic Acetal on Copolymer Backbone

Ethanol

The above techniques utilize aldehyde or ketone flavors. Examples of aldehyde flavors include: acetaldehyde (apple); benzaldehyde (cherry, almond); anisic aldehyde (licorice, anise); cinnamic aldehyde (cinnamon); citral, i.e. alpha citral (lemon, lime); neral, i.e. beta citral (lemon, lime); decanal (orange, lemon); ethyl vanillin (vanilla, cream); heliotropine, i.e. piperonal (vanilla, cream); vanillin (vanilla, cream); α-amyl cinnamaldehyde (spicy fruity flavors); butyraldehyde (butter, cheese); valeraldehyde (butter, cheese); citronellal (modifies, many types); decenal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. Melonal ® (melon); 2,6-dimethyloctanal (green fruit); and, 2-dodecenal (citrus, mandarin). Examples of ketone flavors include: d-carvone (caraway); l-carvone (spearmint); diacetyl (butter, cheese, "cream"); benzophenone (fruity and spicy flavors, vanilla); methyl ethyl ketone (berry fruits; maltol (berry fruits) menthone (mints) methyl amyl ketone, ethyl butyl ketone, dipropyl ketone, methyl hexyl ketone, ethyl amyl ketone (berry fruits, stone fruits); pyruvic acid (smokey, nutty flavors); acetanisole (hawthorn heliotrope); dihydrocarvone (spearmint); 2,4-dimethylacetophenone (peppermint); 1,3-diphenyl-2-propanone (almond); acetocumene (orris and basil, spicy); isojasmone (jasmine); d-isomethylionone (orris like, violet); isobutyl acetoacetate (brandy-like); zingerone (ginger); pulegone (peppermint-camphor); d-piperitone (minty); and, 2-nonanone (rose and tea-like).

Another method for producing compositions of this invention involves reacting alcohol flavors with polymers having pendant aldehyde or ketone groups. This is specifically illustrated as follows:

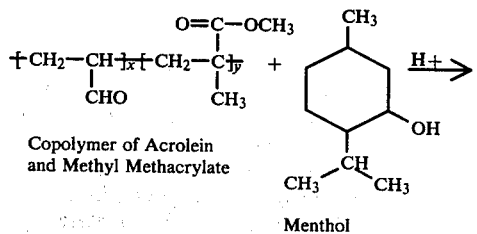

Copolymer of Acrolein and Methyl Methacrylate

Menthol

-continued

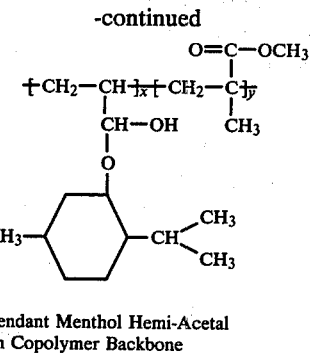

Pendant Menthol Hemi-Acetal on Copolymer Backbone

Some specific examples of alcohol flavors include: anisic alcohol or p-methoxybenzyl alcohol (fruity, peach); benzyl alcohol (fruity); carvacrol or 2-p-cymenol (pungent warm odor); carveol; cinnamyl alcohol (floral odor); citronellol (rose like); decanol; dihydrocarveol (spicy, peppery); tetrahydrogeraniol or 3,7-dimethyl-1-octanol (rose odor); eugenol (clove); and, p-mentha-1,8-dien-7-Oλ or perillyl alcohol (floral-pine).

The sustained flavor release compositions described herein are especially useful in chewing gums. Customarily, chewing gums contain chewing gum base, flavor, sweetener, filler, and certain other optional ingredients.

Chewing gum bases are usually resinous materials and should be non-toxic, clean, odorless, tasteless, colorless, non-sticky, elastic, economical, insoluble in water, resistant to decomposition and depolymerization, resistant to oxidation and embrittlement upon aging, resistant to conversion into toxic products and resistant to flavor dissipation, etc. The primary requirement is, of course, that they impart a permanent chewability to the chewing gum composition. Many natural and synthetic resins have been utilized as chewing gum bases. Chickle is the most widely used natural resin whereas homo- and copolymers of vinyl acetate, sometimes partially hydrolized, are examples of synthetic chewing gum bases. These bases and others customarily used can be used with the sustained flavor release compositions described herein to form chewing gums.

Suitable sweetening agents include sucrose, dextrose, invert sugar, honey, levulose, saccharin, cyclamates, etc.

In like manner, fillers customarily used are also satisfactory. Mineral fillers are used which are finely ground, inert, non-toxic, tasteless and not exceedingly abrasive. In addition, they must not crumble during the chewing process. Inert pigments may also be incorporated into the chewing gum formulations as part of the filler content in order to color the mix. Typical inert pigments and filler materials include: precipitated chalk, clay, barium sulfate, magnesium oxide, silica, talc, carbon black, iron oxide, yellow ochre, magnesium carbonate, calcium sulfate, etc.

Optional additives such as waxes used to lubricate and facilitate the high speed manufacturing process, conditioning agents such as glycerine and propylene glycol, and various medicinal compounds, etc., can, of course, be added to the chewing gum compositions described herein.

The known methods for the preparation of conventional chewing gum products may be employed in preparing chewing gums of this invention. In general, one or more blending operations is required which may be carried out at elevated temperatures followed by the introduction of the homogeneous mass into a mill which forms gum sheets which are subsequently cut into chewing gum sticks.

The proportions of the various ingredients will vary over wide ranges according to the final taste desired. In general, however, it has been found that suitable chewing gums can be prepared using the controlled release flavors of this invention in amounts ranging from about 5% to about 20% by weight.

When used in chewing gum or other flavored products, the sustained flavor release compositions described herein can, of course, be combined with other flavors which may or may not be controllably released. For example, chewing gum formulations can be prepared using some of the controlled release flavors described herein as well as some natural flavors and might even include some of the flavors encapsulated by prior art methods.

The following examples further illustrate the invention. All parts and percentages are by weight unless otherwise specified.

EXAMPLE 1

Preparation of the Cyclic Acetal of Cinnamic Aldehyde and Glycerin

In a one-liter, three-neck round bottom flask equipped with a water cooled condenser, stirrer, and a water separator, 66 g. of cinnamic aldehyde is added to 46 g. of glycerin in 200 ml. of dry benzene containing 2 g. of polyphosphoric acid. After 6.5 hours, 8.5 ml. of water are removed from the separator and 200 ml. additional benzene is added to the reaction mixture. After washing with 300 ml. of 1% sodium hydroxide solution and rinsing until neutral, the mixture is filtered and the benzene is removed under vacuum. The light yellow solid is then vacuum distilled.

Product identification is based in IR, which shows no carbonyl frequency, and mass spec.

Boiling point 170° at 1.8 mm. Hg, Molecular Weight by Mass Spec. 206.

The cyclic acetal so prepared can be named 2-($\beta$-styryl)-1,3-dioxolane-4-methanol.

EXAMPLE 2

Alcoholysis to Tack Cyclic Acetal onto Polymer Backbone

A 128.2 g sample of dried ethyl acrylate-ethylene copolymer containing 50 mole percent ethylacrylate prepared in accordance with the teachings of U.S. Pat. No. 2,953,551, Sept. 20, 1960 in 500 ml. of dry toluene is stirred with 206.3 g. of 2-($\beta$-styryl)-1,3-dioxolane-4-methanol as prepared in Example 1. To this solution is added 2.0 g. of lithium methoxide and the reaction mixture is brought to reflux. After one hour, collection of ethanol distillate is started and continued until the rise in boiling point indicates that no more ethanol is being collected. Close to 46 g. of ethanol, the nearly theoretical amount is obtained. After filtering, the reaction mixture is stripped of toluene at reduced pressure leaving 288.0 g. of an off-white resin. This resin, without further treatment, can be incorporated in chewing gum to the extent of 6 to 10% by weight to provide a cinnamon flavor upon mastication of the gum.

EXAMPLE 3

Alternative Alcoholysis for Tacking Cyclic Acetal onto Polymer Backbone

A 40 g. sample of citrus pectin N.F. in which a high proportion of the D-galacturonic acid moieties are present as methyl esters is dried in a vacuum oven at 50° C. for six days followed by removing the last traces of water with a Dean-Stark trap and refluxing benzene. The reaction mixture is then treated with 17.0 g. of 2-($\beta$-styryl)-1,3-dioxolane-4-methanol (Example 1), 3.0 g. of sodium methoxide, and brought to reflux for one hour. With the condenser set for downward distillation, benzene and methanol are distilled and the process continued until tests of the distillate with 2,4-dinitrobenzoyl chloride show that no more methanol is being generated. The solid precipitate is filtered from the reaction mixture and dried under vacuum. The powder can be incorporated into chewing gum in amounts of 6–10% to provide the slow release of cinnamon flavor on chewing.

EXAMPLE 4

Reaction of Hydroxypropyl Cellulose and Cinnamic Aldehyde to Tack Acetal onto Polymer Backbone In a 100×50 mm. crystallizing dish, 6.7 g. of Klucel ® hydroxypropyl cellulose (Hercules type EF) and 3.7 g. of cinnamic aldehyde are thoroughly mixed. The mixture is kneaded with a spatula to a dough. In portions, 0.5 ml. of 33% by volume HCl solution is worked in. The dough is then pressed between glass plates into a film and the film allowed to stand under nitrogen 24 hours. The film is then placed under vacuum at 80° C. for a four-hour period. After cooling, the product is ground to a coarse powder in a blender.

EXAMPLE 5

Preparation of Chewing Gum from Acetal of Klucel ® and Cinnamic Aldehyde

Chewing gum base is melted in a small double boiler, and the temperature is maintained at approximately 47° C. throughout the formulation.

| Materials (In Order of Addn.) | Amount in Grams |
| --- | --- |
| gum base | 21.0 |
| corn syrup | 7.6 |
| powdered sugar | 13.6 |
| fumaric acid | 1.8 |
| glycerin/water (50/50) | 0.6 |
| corn oil | 0.2 |
| flavor (Ex. 4) | 3.0 |

The hot mixture is poured onto a Mylar ® sheet and rolled between two Mylar ® sheets. The gum is then frozen and the Mylar ® removed. This gum exhibits good flavor release after chewing for one hour.

EXAMPLE 6

Preparation of Copolymer of Acrolein-Methyl Methacrylate.

A two-liter resin kettle equipped with mechanical stirrer, condenser and nitrogen gas inlet is charged with 72.1 g. methyl methacrylate, 10.1 g. acrolein and 23.2 ml. ethyl acetate. The solution, stirred and heated to 90° C. under nitrogen atmosphere, is treated with 1.21 g. Vazo ® in 13.5 ml. of ethyl acetate. To this reaction mixture there is added slowly over a 50-minute period 168.1 g. methyl methacrylate, 23.5 g. acrolein, 2.3 g. Vazo ® catalyst in 156 ml. ethyl acetate. The mixture is stirred for an additional hour at 90° C. becoming viscous and cloudy. With the reflux condenser set for downward distillation, solvent and unreacted monomers are distilled out.

The clear, viscous resin is dissolved in 250 ml. of fresh ethyl acetate. The cooled solution is stirred with a saturated solution of sodium hydrogen carbonate until foaming subsides. The mixture is transferred to a two-liter preparatory funnel and the water layer removed. The reaction mixture is washed again with 300 ml. of water and after separation the white viscous resin layer is subjected to low pressure in a vacuum desiccator to remove the last traces of solvent. The white brittle solid weighed 219.1 g. (an 80% yield) and contained 20 mole % of

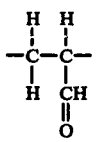

groups. Analysis by infrared spectroscopy confirms the presence of aldehyde groups.

EXAMPLE 7

Preparation of Acetal of Methyl Methacrylate-Acrolein Copolymer

A 91.29 g. sample of dried copolymer (Example 6) is stirred with 300 ml. of toluene, 34.86 g. of hydroxycitronellol, 2 g. of polyphosphoric acid, for two hours at 75° C. After standing overnight at room temperature, the batch is washed two times with 200 ml. portions of saturated sodium hydrogen carbonate followed by water washing. When the solvent toluene is removed under reduced pressure, a brittle resin remains. I. R. spectroscopy confirms that most of the aldehyde groups have been converted to acetal and/or hemiacetal groups. When this resin is incorporated in chewing gum and chewed, a flavor reminiscent of hyacinth rose and grape is slowly released.

EXAMPLE 8

Alternate Method of Acetal Preparation

In a 100×50 mm. dish, 9.13 g. of methyl methacrylateacrolein copolymer is thoroughly mixed with 3.1 g. of 1-menthol and formed into a dough with a minimum amount of dioxane. In portions, 0.5 ml. of 33% hydrochloric acid is worked into the dough. The dough is then pressed into a film between glass plates and allowed to remain under nitrogen for 24 hours. The film is then subjected to low pressure at 80° C. for a four-hour period when most of the solvent, water and hydrogen chloride leave. After cooling, the product is ground to a coarse powder. Infrared spectroscopy confirms the disappearance of aldehyde groups.

What is claimed is:

1. Controlled flavor release compositions comprising a polymer backbone having a pendant flavor moiety thereon, said pendant flavor moiety being releasable from said polymer by hydrolysis and consisting of an acetal, hemiacetal or ketal flavor moiety formed by chemically reacting an alcohol flavor with a polymer having pendent aldehyde or keytone groups, said polymer having a molecular weight of from about 2,000 to about 20,000.

2. A composition of claim 1 wherein said alcohol flavor consists of anisic alcohol (p-methoxybenzyl alcohol); benzyl alcohol; carvacrol (2-p-cymenol); carveol; cinnamyl alcohol; citronellol; decanol; dihydrocarveol; tetrahydrogeraniol 3,7-dimethyl-1-octanol; eugenol; p-metha-1,8-dien-8-Oλ (perillyl alcohol).

3. A composition of claim 2 wherein said polymer consists of a polymer formed from acrolein.

* * * * *